(12) United States Patent
Fonduca et al.

(10) Patent No.: US 9,737,253 B2
(45) Date of Patent: Aug. 22, 2017

(54) PORTABLE MEDICAL APPARATUS INCLUDING SAMPLING, DETERMINING AND INJECTING COMPONENTS

(75) Inventors: Antonio Fonduca, Stockholm (SE); Michael Göran Erik Frantzén, Stockholm (SE); Truls Jonas Ulfstand Sjöstedt, Stockholm (SE)

(73) Assignee: Brighter AB, Stockholm (SE)

( * ) Notice: Subject to any disclaimer, the term of this patent is extended or adjusted under 35 U.S.C. 154(b) by 711 days.

(21) Appl. No.: 12/674,363

(22) PCT Filed: Aug. 29, 2008

(86) PCT No.: PCT/IB2008/053517
§ 371 (c)(1),
(2), (4) Date: Feb. 19, 2010

(87) PCT Pub. No.: WO2009/027950
PCT Pub. Date: Mar. 5, 2009

(65) Prior Publication Data
US 2011/0282173 A1    Nov. 17, 2011

(51) Int. Cl.
*A61B 5/157*    (2006.01)
*A61B 5/145*    (2006.01)
(Continued)

(52) U.S. Cl.
CPC .......... *A61B 5/157* (2013.01); *A61B 5/14532* (2013.01); *A61B 5/150022* (2013.01);
(Continued)

(58) Field of Classification Search
CPC .... A61M 5/002; A61M 5/003; A61M 5/1723; A61M 5/31585; A61M 5/31586;
(Continued)

(56) References Cited

U.S. PATENT DOCUMENTS 4,895,147 A * 1/1990 Bodicky .......... A61B 5/150022
                                                    600/583
5,536,249 A    7/1996 Castellano et al. ............. 604/65
(Continued)

FOREIGN PATENT DOCUMENTS

| EP | 1 571 582 | 9/2005 | |
| WO | WO 2004/030726 A1 * | 4/2004 | ............ A61M 5/142 |
| WO | WO 2006/021051 | 3/2006 | |

OTHER PUBLICATIONS

Switch. (1992). In C. G. Morris (Ed.), Academic Press Dictionary of Science and Technology. Oxford, UK: Elsevier Science & Technology. Retrieved from <http://search.credoreference.com/content/entry/apdst/switch/0> on Jan. 30, 2017.*
(Continued)

*Primary Examiner* — David J McCrosky
(74) *Attorney, Agent, or Firm* — Winston & Strawn LLP

(57) ABSTRACT

A portable medical apparatus including at least a sampling assembly for providing at least one sample of a fluid in an object, a detector for determining at least one parameter of the fluid, an injector for performing at least one injection of an injection medium, and which are operable independent of each other for improved self-treatment of diseases such as diabetes. The portable medical apparatus has a single common housing for these components and a switch for changing between the sampling mode, the determining mode, and the injection mode. The apparatus also includes an actuator means for individually actuating the other components. The apparatus is an all-in-one device that facilitates the medical treatment process for patients, medical professionals or others.

19 Claims, 13 Drawing Sheets

(51) Int. Cl.
  *A61B 5/00*     (2006.01)
  *A61M 5/172*    (2006.01)
  *G01N 33/487*   (2006.01)
  *A61B 5/15*     (2006.01)
  *A61B 5/151*    (2006.01)
  *A61M 5/31*     (2006.01)

(52) U.S. Cl.
  CPC ...... *A61B 5/15113* (2013.01); *A61B 5/15117* (2013.01); *A61B 5/15153* (2013.01); *A61B 5/15163* (2013.01); *A61B 5/150167* (2013.01); *A61B 5/150175* (2013.01); *A61B 5/150358* (2013.01); *A61B 5/150412* (2013.01); *A61B 5/150519* (2013.01); *A61B 5/150748* (2013.01); *A61B 5/4839* (2013.01); *A61M 5/1723* (2013.01); *G01N 33/48785* (2013.01); *A61B 2562/0295* (2013.01); *A61M 2005/3103* (2013.01)

(58) Field of Classification Search
  CPC ......... A61M 2005/1726; A61B 5/1411; A61B 5/14532; A61B 5/15156; A61B 5/20; A61B 5/150267; A61B 2562/0295; A61B 5/157; A61B 5/150519; A61B 5/15113; A61B 5/15115; A61B 5/15148–5/15178; A61B 5/4839
  USPC .... 600/309, 365, 583, 584; 604/65–67, 187, 604/188, 191–197, 207, 208, 890.1, 891.1
  See application file for complete search history.

(56) References Cited

U.S. PATENT DOCUMENTS

| | | | |
|---|---|---|---|
| 5,593,390 A | 1/1997 | Castellano et al. | 604/187 |
| 5,728,074 A | 3/1998 | Castellano et al. | 604/207 |
| 5,810,199 A | 9/1998 | Charlton et al. | 221/31 |
| 5,925,021 A | 7/1999 | Castellano et al. | 604/207 |
| 6,192,891 B1* | 2/2001 | Gravel et al. | 604/187 |
| 6,302,855 B1 | 10/2001 | Lav et al. | 600/584 |
| 2002/0019296 A1* | 2/2002 | Freeman et al. | 482/4 |
| 2004/0068230 A1* | 4/2004 | Estes et al. | 604/154 |
| 2005/0192494 A1 | 9/2005 | Ginsberg | 600/365 |
| 2006/0008389 A1* | 1/2006 | Sacherer | A61B 5/15146 600/583 |
| 2006/0100543 A1* | 5/2006 | Raney et al. | 600/583 |
| 2006/0161078 A1* | 7/2006 | Schraga | 600/583 |
| 2007/0009381 A1* | 1/2007 | Schulat | G01N 33/48757 422/400 |
| 2007/0173739 A1* | 7/2007 | Chan | G01N 33/48757 600/583 |
| 2007/0179435 A1 | 8/2007 | Braig et al. | 604/66 |
| 2007/0179436 A1 | 8/2007 | Braig et al. | 604/66 |
| 2007/0219572 A1* | 9/2007 | Deck | A61B 5/15113 606/181 |
| 2007/0265511 A1 | 11/2007 | Renouf | 600/319 |
| 2008/0007141 A1* | 1/2008 | Deck | H02N 2/043 310/328 |
| 2008/0015623 A1* | 1/2008 | Deck | A61B 5/15146 606/181 |
| 2008/0269585 A1 | 10/2008 | Ginsberg | 600/365 |
| 2008/0312604 A1* | 12/2008 | Boesen | 604/207 |
| 2009/0182244 A1* | 7/2009 | Hoenes | G01N 33/48778 600/583 |
| 2009/0192367 A1 | 7/2009 | Braig et al. | 600/311 |

OTHER PUBLICATIONS

International PreliminaryReport on Patentabilityand Search Report, PCT/IB2008/053517, mailed Jun. 23, 2009.

\* cited by examiner

US 9,737,253 B2

PORTABLE MEDICAL APPARATUS INCLUDING SAMPLING, DETERMINING AND INJECTING COMPONENTS

This application is a 371 filing of International Patent Application PCT/IB2008/053517 filed Aug. 29, 2008, which claims the benefit of application No. 60/968,763 filed Aug. 29, 2007.

BACKGROUND

The present invention relates to a portable medical apparatus including at least a sampling means for, in a sampling mode, providing at least one sample of a fluid in an object, a determining means for, in a determining mode, determining at least one parameter of the fluid, an injecting means for, in an injecting mode, performing at least one injection of an injection medium, and which means are operatable independent of each other or in co-operation with each other.

Many treatment regimes require continuous monitoring of one or more parameters in a fluid in response to which parameters self-treatment can be performed. A typical example of self-treatment is injection of a suitable amount of insulin in response to determination of the glucose concentration in a blood sample of a diabetic patient.

However, a general problem of such known devices is that they are not sufficiently user friendly. The reasons for this are that in many cases, several pieces of equipment have to be carried, operated and maintained to fulfill the need of analyzing and acting upon the analysis. For example in the above self-treatment of diabetes many diabetics needs to carry and use the following equipment: lancer including lancets to take a blood sample, glucose meter including test strips for determining the glucose concentration in the blood sample, an insulin ampoule, and a means for injecting insulin, typically in the form of a pen or syringe.

These disadvantages are attempted solved by means of the multifunctional device disclosed in U.S. Pat. No. 6,302,855 B1. This known device is a collection of some of the plurality of sub-devices, which the diabetic needs in the self-treatment. Each sub-device has its own dedicated function and all sub-devices are mutually interconnectable to provide a portable but bulky combined device, which takes op considerable space when brought along. Also, there is a risk that one device is forgot after use. If the absence of a sub-device not is discovered before the next time the multifunctional device is to be used it can be crucible to the patient who is prevented from performing at least the step of the missing sub-device, which step is essential for performing the entire series of step for the self-treatment.

Thus, there is a need within self-treatment procedures for a reliable, small and easy operatable device or apparatus not suffering from the above disadvantages.

SUMMARY OF THE INVENTION

Accordingly, it is a main aspect of the present invention to provide a portable medical apparatus of the kind mentioned in the opening paragraph in which a plurality of functions are integrated in a common housing to provide an integrated compact structure.

It is a second aspect of the present invention to provide a portable medical apparatus of the kind mentioned in the opening paragraph, which apparatus combines the functionality and benefits of several devices used in the process of analyzing a sample of a body fluid and acting upon the outcome of the analysis.

It is a third aspect of the present invention to provide a portable medical apparatus of the kind mentioned in the opening paragraph, which apparatus facilitates medical treatment processes performed by patients, medical professionals and/or other persons.

It is a fourth aspect of the present invention to provide a portable medical apparatus of the kind mentioned in the opening paragraph, which apparatus is easy and fast to adjust and switch between different functionality modes.

It is a fifth aspect of the present invention to provide a portable medical apparatus of the kind mentioned in the opening paragraph, that combines the functionality and benefits of several devices used in the process of analyzing and act upon the outcome of the analysis into a single portable unit.

It is a sixth aspect of the present invention to provide a portable medical apparatus of the kind mentioned in the opening paragraph, that unite three traditionally separated devices into one pocketsized device to make a medical procedure easier to carry out.

It is a seventh aspect of the present invention to provide a portable medical apparatus of the kind mentioned in the opening paragraph, that is more portable and easy to maintain than existing solutions.

The novel and unique features whereby this is achieved is the fact that the apparatus, further comprises a common housing for at least the sampling means, the determining means and the injecting means, a switching means for switching between at least any of the sampling mode, the determining mode, and the injection mode, and actuation means for individually actuating at least one of the sampling means, the determining means and the injecting means.

By enclosing the sub-devices, i.e. at least the sampling means, the determining means and the injecting means in a single common housing the apparatus appears as an integrated structure allowing the user to always have the sub-devices ready at hand for use. The switching means beneficially serves for switching between the various functionality modes according to need. Thus, if for example sampling is required the switching means is used for configuring the apparatus to the required functionality mode and the actuation means is actuated to perform the required act. A typical series of steps includes first to choose the sampling mode using the switching means and actuating the actuation means to puncture the object in order to obtain a fluid sample, e.g. a drop of blood. Next using the switching means to choose the determining mode and actuating the determining means by means of the actuating means to determine a determinable parameter of the fluid sample, e.g. the glucose concentration in drop of blood, and in response to the determined parameter, in this case the glucose concentration, using the switching means to chose the injection mode and performing an injection of an injection medium by actuating the injecting means.

The single common housing advantageously keeps the sub-devices assembled so that they cannot be unintentionally separated, as is the case with the prior art devices.

The apparatus may comprise a processing unit for controlling the functionality modes of the apparatus. In the sampling mode the processing unit may for example control or adjust the power used for obtaining the sample, i.e. the sampling stroke or lancing force.

Stroke depths of for example 2 mm or 3 mm may require different stroke forces. An adjustable stroke force can for example be created using the pressure from a gas cartridge, a mechanical lengthwise adjustment of the actual position of the lancets tip by means of a battery powered motor inside the common housing, or manual tension of a compression spring means which, once released, forces the lancet tip towards the target object. The adjustable stroke force may also be achieved by combinations of one or more of these means as well as any of such means also may by used for adjusting the injection power of the injecting means. Thus, in a very simple embodiment the injecting means and the sampling means shares one or more common parts.

The sampling force is adjustable not in steps only but also on a continuous scale, thereby better adjusting to any specific user's needs. The skilled user will appreciate that adjustment of the lancing force is continuous.

In the present invention the terms sampling force and lancing force is used interchangeable.

Another function of the processing means is to control the determination process of the parameter and, if desired, possibly calculate a suitable dose of injection medium to be injected based on the value of the determined parameter, and to transmit information of the suitable dose to the user.

The processing unit may also provide everyday information, such as date, day, clock, etc. to the user to keep him/her continuously updated. Information of relevant and actual functionality modes and status of the apparatus makes the use of the apparatus easy and reliable and prevent incorrect use.

Preferably the apparatus according to the invention can contain an audible, vibrational or otherwise noticeable alarm that can be set for an individual number of medication reminders a day.

The processing unit may be a central processing unit such as an Integrated Circuit which, using todays technology, can be on the order of nanometers, e.g. as used in todays mobile phones. Thus the processing unit does not take up much space inside the common housing. A data storage means may be provided to allow the user to store data in relation and response to use. The apparatus may further include means for remote programming the processing unit and reading the stored data. A physician or any other qualified person may conveniently perform such operations. Thus, the use of the inventive apparatus according to the present inventions discloses not yet previously disclosed prospects in performing and monitoring self-medication and self-treatment of many diseases. The apparatus allows a physician to interact in the self-treatment regimen if necessary, for example in a training period, or if the parameter level of the user is difficult to adjust and/or the determined parameters fluctuate a great deal.

The apparatus can preferably include one or more adjusting means for adjusting at least one of the sampling means, the determining means and the injecting means according to individual needs and choice of functionality mode. By using such adjusting means the apparatus can easily be configured to have and preserve a standard configuration, which is the most preferred by the user, or be adjusted ad hoc. Ad hoc adjustment may take place based on data stored in the storage means, calculated and transmitted by the processing unit, or be made manually in case the processing means serves for ad hoc control of the adjusting means and change of configuration of the apparatus to new functionality modes and conditions before and after each operation if the treatment regime requires such adjustment. The adjusting means may be part of the actuation means and/or the processing means.

In an optimal embodiment of the apparatus according to the present invention the apparatus may be arranged for operating the injecting means in response to the determined parameter. For example, the processing unit establishes by calculation or by table look-up the appropriate dose of injection medium to be injected in response to the determined parameter of the fluid to alleviate, remedy or regulate the level of said determined parameter in the fluid of the object at least until the next time the sampling mode and determining mode must be carried out. To this aspect the apparatus may include an alert means expediently controlled by the processing means to call the users attention to repeat the use of the apparatus. The processing means may de designed to predict when repeated use takes optimum place, at intervals having the same or different lengths etc.

A preferred user friendly design of the common housing included a hollow body having a first part capped by a an exterior part of the actuation means, which first part opposite the exterior part is in operative communication with a second part optionally via at least the switching means, said second part has an operating end from which any of at least the sampling means, the determining means and the injecting means can be exposed to interact with either the object or one of the other means. The first part is the part of the elongated common housing of the apparatus that rests in the palm of the hand during use to easy access the exterior part of the actuation means e.g. using the thumb to depress said exterior part. The second part is the part pointing towards the object during use. The second part of the common housing may among other things encase the injection medium, the determining means, the sampling means and the injecting means all of which at some stage during operating the apparatus need interaction with the object.

The cross sectional area of the first part and the second part is preferably the same and circular, but within the scope of the present invention a plurality of other shapes are foreseen, as well as the second and first part may have different cross-sectional areas or different exterior surfaces for making the first and second part tactile distinguishable from each other, as may be a welcome feature for anybody but in particular for visually handicapped or otherwise impaired users. Thus also oval, elliptic and even squared cross-sectional areas may be preferred by some user to keep the apparatus completely still during use and operation and to identify a specific part of the apparatus. The exterior design of the common housing may be provided with one or more individual or sets of depressions or protrusions to provide indication to the user of which functionality mode is presented to him/her. The depressions or protrusions are intended to facilitate locating a presented functionality mode with the fingers and to keep a selected functionality mode, position and orientation of the apparatus during use. In addition various kinds of color indications may be used to enhance user friendliness.

By locating the switching means in proximity to both the first part and the second part the same switching means can be used for operating both parts while still being kept in communication.

In a preferred embodiment the first part is rotatable in opposite direction to the second part along a longitudinal axis of the common housing, which rotatable arrangement constitutes at least a part of the switching means. Thus, by rotating the first part of the common housing in relation to the second part of the common housing switching between the different functionality modes is achieved. Depending on whether the user is right or left handed the apparatus is set by said user using the programming unit and the switching means so that the first part and the second part is rotated either counter-clockwise or clockwise, respectively, or vice versa if this configuration is more preferred. In a preferred embodiment the longitudinal axis is common to both the first and the second part.

To assure and to provide an indication that switching between different functionality mode has taken place or is in progress of taking place the switching means may comprises at least one sensor for registrating switching between at least the sampling mode, the determining mode and/or the injection mode. The sensors may for example be optical sensors, electronic sensors such as contact sensor, a noise indicator which illicit a noise when opposing contacting mechanical parts of the first and second part passes each other during rotation, or a stepwise interlocking of the two parts once a functionality mode has been reached and which interlocking must be manually released.

In any of the above discussed and suggested situations information about the switching process between the functionality mode, the rotation direction and degree and any other current status of at least the apparatus may be displayed on a display. Preferably the display is located at the first part of the common housing to display relevant information to the user without the display gets soiled and visualization being impaired. The display can however within the scope of the present invention be provided anywhere appropriate in relation to the apparatus and may also be used for controlling the apparatus via a touch screen. A set of standard information is basic for the apparatus but the user may individualize the degree of information by suitable programming of the processing unit to keep the user updated of any important data to remember and information required for optimizing the self-treatment.

The second part, optionally opposite the switching means, may preferably be closed by an end part having at least one opening for exposure of at least the sampling means, the determining means and the injecting means. In this embodiment residues given off from the object when sampling, determining and injecting are prevented from getting inside the common housing. Blood splashing and injection medium splashing are sometimes experienced by a user and if such liquid content get in touch with the mechanical movable parts and/or electronics parts inside the common housing the functionality and operability of the apparatus may be affected and eventually the apparatus becomes unreliable. The same disadvantages are seen if humidity, as vapors or liquid water or other fluids etc., enters the common housing. The electronic parts may thus short-circuit and mechanical parts malfunction due to the deposits simply obstructing the movements of said mechanical parts. In order to allow substitution and replacement of used, expired and/or defect parts and means located inside the second part the end part may be designed to be opened, preferably by designing the end part with a detachable lid or cap which is screwed on or capped on the operating end of the second part.

In order to direct the operating end of the second part of the apparatus in the right direction and to overview the various operations and manoeuvre the operating end of the second part, the apparatus may advantageously be provided with an illumination means for illuminating at least a part of the object. A small bulb or LED may serve the purpose if situated at the operating end. Illumination means could in the alternative be provided alongside the common housing instead or any other appropriate location on the apparatus.

The apparatus may conveniently be powered by a power source located inside the common housing, typically a disposable or rechargeable battery inside the first part of the common housing. The battery is replaced via an opening in the first part of the common housing, and/or recharged through a connection means such as a USB connection.

A rotation ring in operative communication, either directly or indirectly, with at least one of the sampling means, the determining means, the injecting means, the actuation means, the processing unit, the storage means and/or the display alone or in combination may serve as a joy-stick for navigating around stored data and other stored information which are relevant to the user and to be shown on the display, as well for making selections, adding user input and programming the apparatus.

The rotation ring is operable along a longitudinal axis of the common housing in at least one longitudinal direction and/or rotatable about the longitudinal axis in at least one rotational direction. Thus the rotation ring may be navigated in for example four different directions, including towards the two longitudinal ends of the common housing, and clockwise and counter-clockwise to the longitudinal axis of the common housing, to scroll along various kinds of information derivable from the processing unit and/or stored in the storage means. As additional information the apparatus may feature an inbuilt calendar and/or clock to provide information to the user of the actual time of year, month, date and hour at the date. A pocket calculator may also be integrated in the processing unit, in which case the rotation ring serves to enter data and perform mathematical functions. This may be relevant in case the user needs to manually recalculate a dose of injection medium, such as a medicament, in response to information unavailable or not yet available in the apparatus at the time of use. For example, a diabetic may need more or less insulin if sudden extensive exercises or special food intake has been made. If this change of metabolic status is not yet determinable in the fluid of the user, e.g. in a blood sample, but the user knows or feels that adjustments need to be done instantaneously he/she uses the calculator to easily calculate the level of adjustment or uses the rotation ring to retrieve data experienced by the user itself in a similar situation. Such data is conveniently logged and stored to establish a personal database and diary as basis of experience for the self-treatment. Games, stopwatch, timer, alarms, positioning systems, and other computer systems are other expedient facilities that may be integrated in the inventive multifunctional apparatus and are foreseen within the scope of the present invention but this list is not intended to be exhaustive. Integration of a tracking system would for example allow the user to be tracked in case of collapse and/or loss of consciousness.

The interior space of the common housing is utilized at its optimum if at least the sampling means, the determining means and the injecting means are located in the common housing alongside or concentric to each other, optionally sharing a common axis.

If at least the sampling means and at least a first part of the determining means are combined in a replaceable cartridge configured to be accommodated in the second part of the common housing user friendliness is very high and hygienic conditions excellent. In the alternative the cartridge could be provided at other suitable location inside the common housing.

The cartridge constitutes a separate unit including a portion of at least the sampling means and at least a first part of the determining means for repeated use in a predetermined period. When the cartridge is all used up, is expired or malfunctions it can easily be removed from the second part of the common housing, for example by opening or removing the end part of the second part and replace the old cartridge with a new one. Alternatively there may be a closable opening in the circumferential wall of the first or second part of the common housing through which the cartridge may be replaced. The elements inside the cartridge are operatable from outside the cartridge interacting with any of the appropriate means inside or outside the common housing including the actuation means which is in operative communication with the sampling means located inside the cartridge and the determination means. The closeable opening in the circumferential wall of the common housing may also serve for replacing other items located inside the apparatus, including repairing the apparatus using spare parts. Also injection medium may be replaced this way.

A preferred design of the cartridge is a cylindrical and/or otherwise tubular body having a hollow circumferential wall chamber holding at least a part of the sampling means and optionally a part of the determining means, which circumferential wall chamber defines a through-going bore chamber for accommodating a reservoir for an injectable medium or to provide access to said reservoir. This arrangement advantageously maximizes use of space.

The through-going bore may serve as a guide means for a part of a replaceable injection means, such as a detachable injection needle, when said injection needle is brought in fluid communication with the reservoir for an injectable medium. Each time an injection needle has been used it may be replaced. To this aspect the through-going bore chamber expediently serves as a guide means for a new, preferably capped, injection needle which is placed on the reservoir configuring the injecting means to dispense and inject a dose of injection medium in response to a determined parameter. Due to this safe guidance of the injection needle in fluid communication with said reservoir for injectable medium the injection needle replacement is very safe and the risk of unintentional or accidental needle pricks is minimal.

The reservoir and the injection needle communicate via an outlet in the reservoir. To prevent leakage from the reservoir the outlet may have a valve mechanism, which valve mechanism closes once the injection medium is detached from the reservoir to be disposed of, which valve mechanism opens once a new injection needle is attached. Alternatively, the hollow injection needle is pointed in both ends, and the valve mechanism at the outlet of the reservoir is a membrane or rubber seal, which a sterile end of the specially designed injection needle facing the reservoir penetrates to provide fluid communication between reservoir and injection needle. Once injection is completed the injection needle may be detached and disposed. The inherent elastic memory of the rubber material of the seal or membrane induces automatically closure of the penetration made in the membrane or rubber seal. Other ways of attaching, detaching and replacing the injection needle may be utilized depending on the design of the cartridge and the injecting means. If for example the injecting means are located parallel to the cartridge replacement of an injection needle may take place using the previously described opening in the circumferential wall of the second part of the common housing.

The sampling means may beneficially include a plurality of circumferentially, linearly and/or randomly distributed lancets. The lancets may advantageously be configured to protrude from the second part to, in response to actuation of the actuation means, making a prick or small incision in an object to gain a sample of fluid for determining a parameter of said fluid. The circumferential distributed arrangements are especially simple to use. The sampling mode is selected, the exterior end part of the actuation means is activated to expose a lancet tip from a cartridge, the same exterior end part of the actuation means is activated once more and the tip of the lancet is forced into the object to make the lesion. Once again the exterior part of the actuation means is activated to retract the lancet tip inside the cartridge to be stored until all lancets in a single cartridge is used. Alternatively the lancets may be disposed directly by pulling it free of the cartridge.

Switching between functionality modes may take place either so that any of the lancet tip, test strip or injection needle, etc. is exposed immediately upon switching, or exposure of the lancet tip, test strip, injection needle, etc. takes place only after an initial activation by e.g. pushing the exterior end part of the actuator means.

The determining means may include a plurality of test strips, optionally disposed alternating with a corresponding number of lancets in the circumferential wall chamber of the cartridge. Other arrangements than alternating may be foreseen within the scope of the present invention. After the lesion has been made, using a lancet as described above, a sample of fluid, e.g. blood, appears on the object. If the fluid is blood the object may be a human or animal. The determining mode is selected using the switching means by rotation of the first part and the second part of the common housing in opposite directions. Once the determining mode is located the exterior end part of the actuation means may be activated to expose a test strip, which is contacted with the sample fluid. The test strip may be of the kind, which contains one or more chemicals that react with a constituent of the fluid sample to determine a level of a parameter to be tested and analysed in the fluid sample. In case of a diabetic the fluid is a blood drop obtained by forcing the lancet into the skin of the diabetic. The parameter of interest in the blood drop is the glucose concentration. The test strip may in this assay have a small spot impregnated with glucose oxidase and iodine to create a color reaction which can be registered. The intensity of the developed color is proportional to the glucose concentration and may be registered by a glucose meter inside the common housing, optionally in the disposable cartridge. Each test strip can only be used once and is then discarded or retracted inside the cartridge in the same manner as described for the lancets.

Accordingly, the lancets and/or the test strips may be displaceable in both directions along a longitudinal axis of the common housing. The lancets and/or the test strips may either be retractable to be isolated into the cartridge after use or the lancets and/or the test strips may be extractable from the cartridge to be discarded after use.

As mentioned above the determining means may include a measuring device for reading the parameter. The measuring device may be is integrated or not integrated in the common housing.

A typical measuring device is a glucose meter. If the glucose meter is of the kind, which is not integrated in the common housing, it may be used to calibrate another integrated glucose meter from time to time or whenever considered appropriate. The not integrated glucose meter may also be the sole glucose meter. Irrespective of which kind or if both kinds of glucose meters are used they are designed to transmit the determined signal or measurement to the processing unit for calculation of an indication reflecting the parameter to be monitored, in this case glucose concentration. Then the processing unit may calculate the exact dose to be injected to adjust the level or concentration of the parameter in the object at the given time of sampling. By rotating the exterior part of the actuation means the injecting means are set to inject the calculated dose of injection medium. Injection takes place by depressing the same exterior part of the actuation means. Conveniently, the exterior part of the actuation means, which is arranged both to be displaceable along and rotatable about the longitudinal axis of the common housing, is a multifunctional knob having a pattern on the exterior surface to enhance grasping force and grasping capability.

In case of a diabetic the injectable medium is insulin or an insulin derivate, which is injected at a suitable dose which may be calculated on the basis of a determination of the glucose concentration in a blood sample of the diabetic. Initially manual setting of the dose will be an alternative and often-preferred method of choice for most users since this is what they have been used to with known devices.

In addition to being a human or an animal the object may also be a plant. As examples of plants sugar cane, trees and citruses can be mentioned all of which have a certain degree of sweetness, which for example can be followed and altered by suitable treatment and nutrition of both the individual plant to be observed, the soil or the water that is admitted to the plant.

When the apparatus is not in use the standby mode may be chosen. In order not to put stress on the user and make it more convenient to navigate between the functionality modes it may take a few seconds, e.g. 1 or 2 seconds, before the display gradually starts going off and enters the stand by functionality mode. To select the stand by functionality mode the user again simply rotates the first part and the second part of the common housing in opposite directions as described above.

In information functionality mode the user can browse, using the rotation ring, through information stored in the storage means and access additional functionality, such as calculators and alarms. The display is activated, lit and visible through a shell.

The information to be displayed may comprise data selected from the group comprising functionality mode, date, clock, the determined parameter, an indication reflecting the status and/or level of the parameter, the amount of medium to be injected in response to the determined parameter, information about the user, status about the apparatus, and power level of the power source and combinations of these, but any kind of information may be displayed.

If one or more of the sampling means, the determining means and the injection means is/are integrated in each other the interior space of the common housing may be utilized at its optimum and the apparatus becomes very easy to use.

In a preferred embodiment according to the present invention the hollow body is a tubular body, preferably an elongated tubular pen. Alternatively the hollow body can be box-shaped or disc-shaped.

It will be appreciated by current users that the apparatus is adapted to be configured to either a right hand mode or a left hand mode.

BRIEF DESCRIPTION OF THE DRAWINGS

The apparatus according to the present invention will now be described in further details below by way of exemplary embodiments with references to the drawing, in which.

DETAILED DESCRIPTION OF THE INVENTION

In the following it is assumed that the apparatus is shaped as a pen however other exterior designs are also intended within the scope of the present invention.

Figure 1:
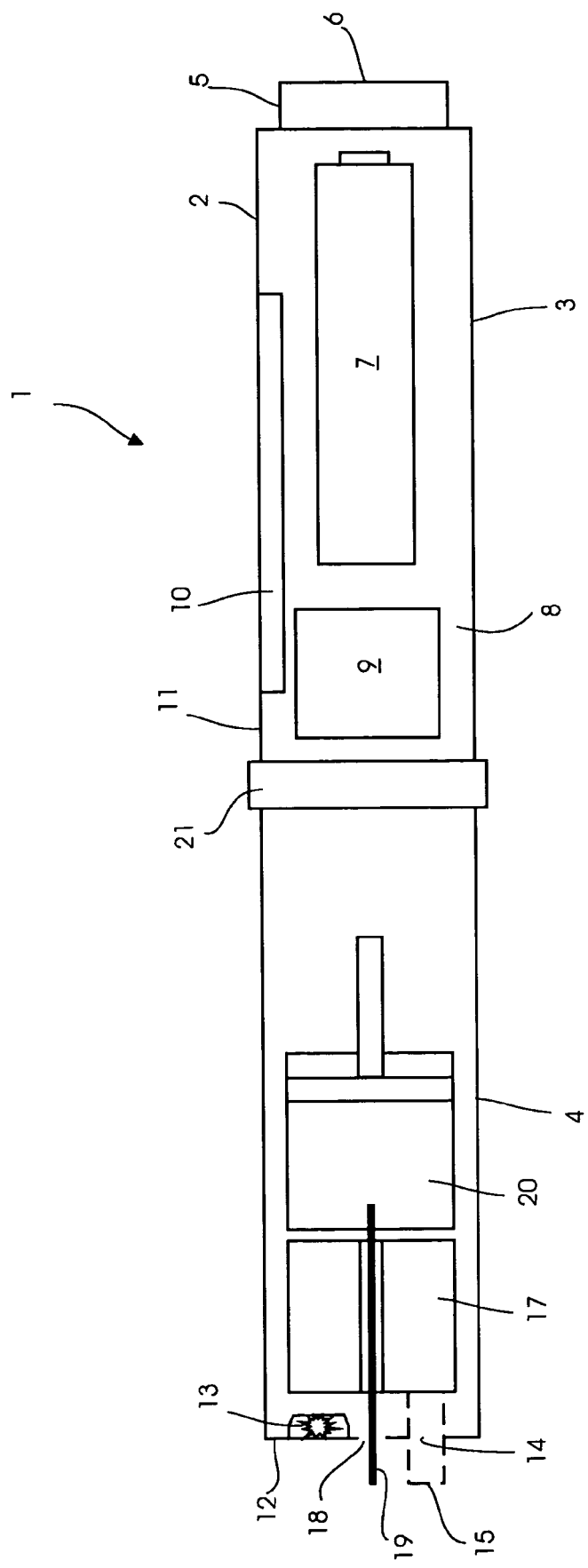
FIG. 1 shows diagrammatic the main parts of an embodiment of an apparatus according to the present invention.

FIG. 1 shows diagrammatic the main parts of an embodiment of an apparatus 1 according to the present invention. The main parts are an elongated, tubular, common housing 2, defined by a first part 3 and a second part 4. The first part 3 has and exterior end part 5 which is a part of the actuation means. The exterior end part 5 is designed as a single multi-functional, rotatable and lengthwise along the longitudinal axis displaceable, knob or button 6 serving to adjust and control several functions depending on functionality mode, including but not limited to adjusting lancing force and depth by rotating the knob,
launching lancet by depressing or pushing the knob in the sampling mode,
adjusting medication dosage by rotating the knob in the injection mode, and
injecting medication by pushing the knob in the injection mode.

The feature of a multifunctional knob enables a cleaner and more user-friendly design. Moreover, it is possible to adjust lancet penetration depth for the medication injection needle using only one needle length. The actuation means supports different penetration depths due to cradle instead of using separate needles, thereby better adjusting to any specific user's needs. The apparatus also allows continuous adjustment of medication volume. Thus medication volume is adjustable not only in steps but on a continuous scale.

A power source in the form of a battery 7 for powering the apparatus 7 is disposed inside the hollow space 8 of the first part 3. The first part 3 also houses a processing unit 9 and other electronic components. A display 10 is provided in the circumferential wall 11 of the housing 2, which display 10 is in electronic communication with the processing unit 9 or any other suitable electronic parts, for example an electronic data storage means, which again is in electronic communication with any of the parts of the apparatus to enable mechanical control and electronic communication with said parts and provide displayable information.

Opposite the exterior end part 5 of the first part 3 of the common housing 2 the first part 3 extends into the second part 4, which second part 4 terminates in an operating end 12 having an illumination means 13, such as a small bulb, to aid the user in poor lighting conditions, a first opening 14 for exposing a test strip 15 or a lancet 16 from a cartridge 17 located inside the second part 4 of the common housing 2, as indicated in dotted line, and a second opening 18 for permitting exposure of an injection needle 19 in communication with a medicament ampoule or vial 20 also located inside said second part 4. A glucose test strip solution and a glucose meter may be accessible to the test strip 15 inside or outside the cartridge 17 (not shown). The ampoule or vial 20 may be designed for use with a specialized ampoule needle 19, which may be snapped on as opposed to screwed on, thereby simplifying the exchange procedure, or it can be adapted to be used with conventional needles having common Luer lock hubs, either screw-threaded or made to conical fit around a corresponding protruding spout and/or valve means.

The combination of a testing/analysis kit and lancets 16 in one exchangeable unit, the cartridge 17, allows for easier and more automated usage as well as lower maintenance and easier refills. For instance, a diabetic may benefit from using refill packages or cartridges consisting of both lancets 16 and glucose test strips 15.

In use the switching means is enabled by rotating two major parts, the first part 3 and the second part 4 of the common housing 2 in opposite directions. This will make the apparatus 1 to switch from one functionality mode to another, thereby making it quicker and easier to access different sets of functionalities.

A rotation ring 21 serves similar function as a joystick to provide a flexible and intuitive navigation system for retrieving and navigating the information stored in an electronic accessible suitable storage means, which storage means can be of any suitable kind. Thus the rotation ring 21 can be a four-way navigation. The user can turn the content of the display 180 degrees, thereby supporting both right and left handed usage in a natural way. The rotation ring 21 may in an alternative embodiment be a pressure button integrated in the circumferential wall. The pressure button may be curved, flat, slightly elevated, or have identifications areas and be designed so that pressure on different spots enables navigation on the display corresponding to using the arrow keys in a computer keyboard. Other modifications of navigation system are within the scope of the present invention.

Figure 2:
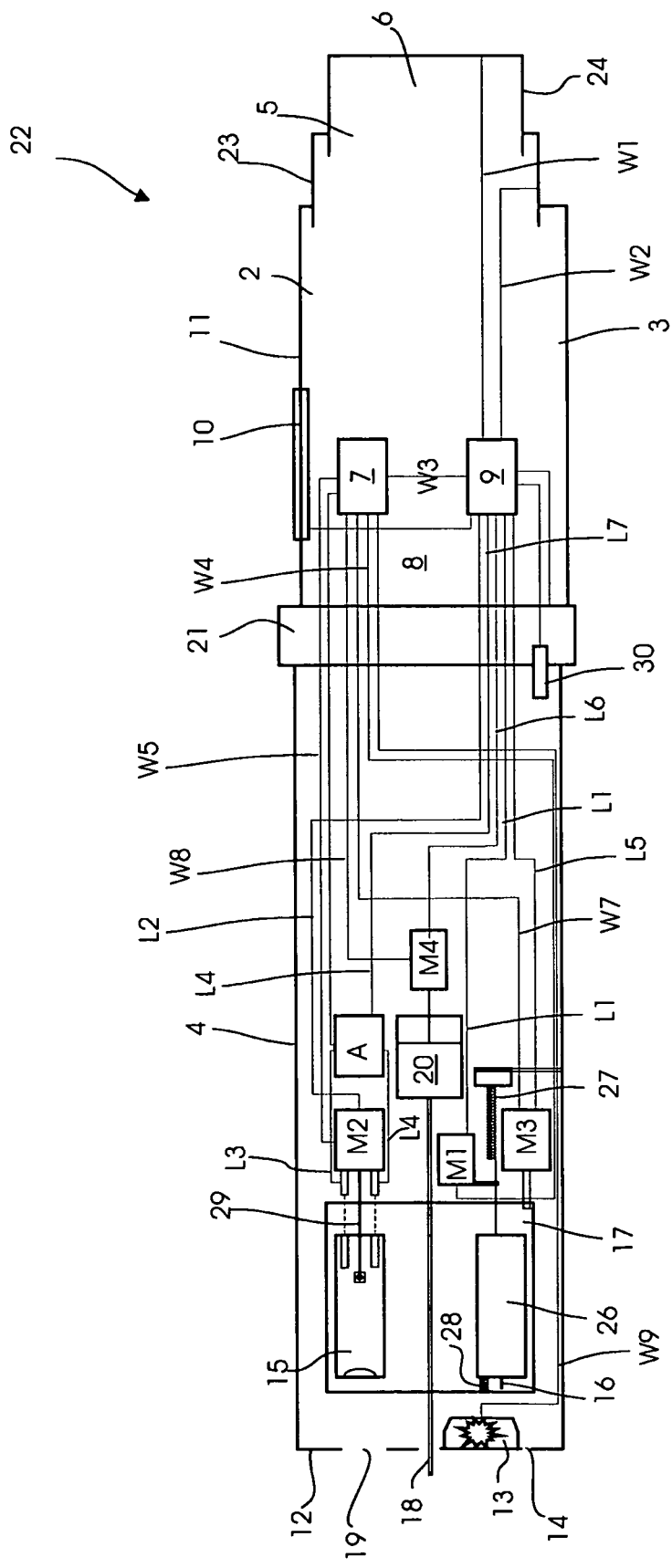
FIG. 2 shows a diagrammatic representation in more details of another embodiment of the apparatus according to the present invention.

FIG. 2 shows a diagrammatic representation in more details of another embodiment 22 of the apparatus according to the present invention. The main parts are substantially the same and for like parts same reference numerals are used.

The apparatus 22 differs from the apparatus 1 in that the exterior part 5 of the actuation means consist of two knob parts, a rotation knob 23 and a function knob 24. The rotation knob 23 serves to stepwise or stepless adjusting operational parameters such as lancing depth, injection force, dosage of medicament etc., and the function knob 24 serves for actuation of lancet stroke, injection stroke, exposure of test strip and optionally also retraction of test strips 15 and/or lancets 16 after use.

The function button 24 of the actuation means 5,6 is in electronic communication with the processing unit 9 via wire W1 and the rotation button 25 is in electronic communication with the processing unit 9 via wire W2. The processing unit 9 is powered by the battery 7 via electric supply line W3.

The battery 7 also via wire W4 provides power to a first motor M1 that loads a lancing device 26 by adjusting the force of a first spring 27 in response to a signal from the processing unit 9 via line L1. Once the first spring 27 is released the lancing device 26 quickly ejects the tip of a lancet 16 from the opening 14 until an opposite acting second spring 28 returns the lancet 16 to its starting position inside a lancing device 26 of a disposable cartridge 17. Alternatively, there may also be a hook (not shown) that can be released instead of releasing the force of the motor M1, in which case the lancet 16 can be removed to be disposed after use.

A second motor M2 controls the arm 29 that hooks and maneuvers the test strip 15. Motor M2 is powered by battery 7 via wire W5 and is controlled by processing unit 9 via line L2. The test strip 15 is in communication with a measuring device, analyzer A, via respective lines L3, L4, which analyzer may be a glucose meter including appropriate chemicals. Thus the analyzer A constitutes an analyzing unit for reading test values of test strips 15. The analyzer A is powered by battery 7 via wire W6 and in communication with processing unit via line L4 enabling information to be registered and processed by the processing unit 9 and optionally stored in a data storage (not shown).

A third motor M3 rotates the entire cartridge 17 to shift at least between functionalities of the sampling mode and the determining mode. Motor M3 is powered by battery 7 via wire W7 and is controlled by processing unit 9 via line L5.

A fourth motor M4 controls the functionality of the injection mode which pushes insulin through the injection needle 18. Motor M4 is powered by battery 7 via wire W8 and is in electronic communication with the processing unit via line L6.

Further the analyzer is in electronic communication with the processing unit 9 via line L7.

The functionality of the above-mentioned motors M1, M2, M3, M4 may alternatively be combined into a single common motor, or two or more motors may be combined for use in controlling parts of the apparatus. The motors forms part of the actuation means 5.

The bulb 13 is also powered by the battery 7, in the case shown via wire W9.

The processing unit 9 is in electronic communication with the rotation ring 21 via a controller 30, which has one or more sensors that monitors any rotation of the first part 3 and the second part 4.

Only one test strip 15 and one lancet 16 are indicated in the schematic drawing of FIG. 2 although a plurality may be enclosed in the cartridge 17.

Figure 3:
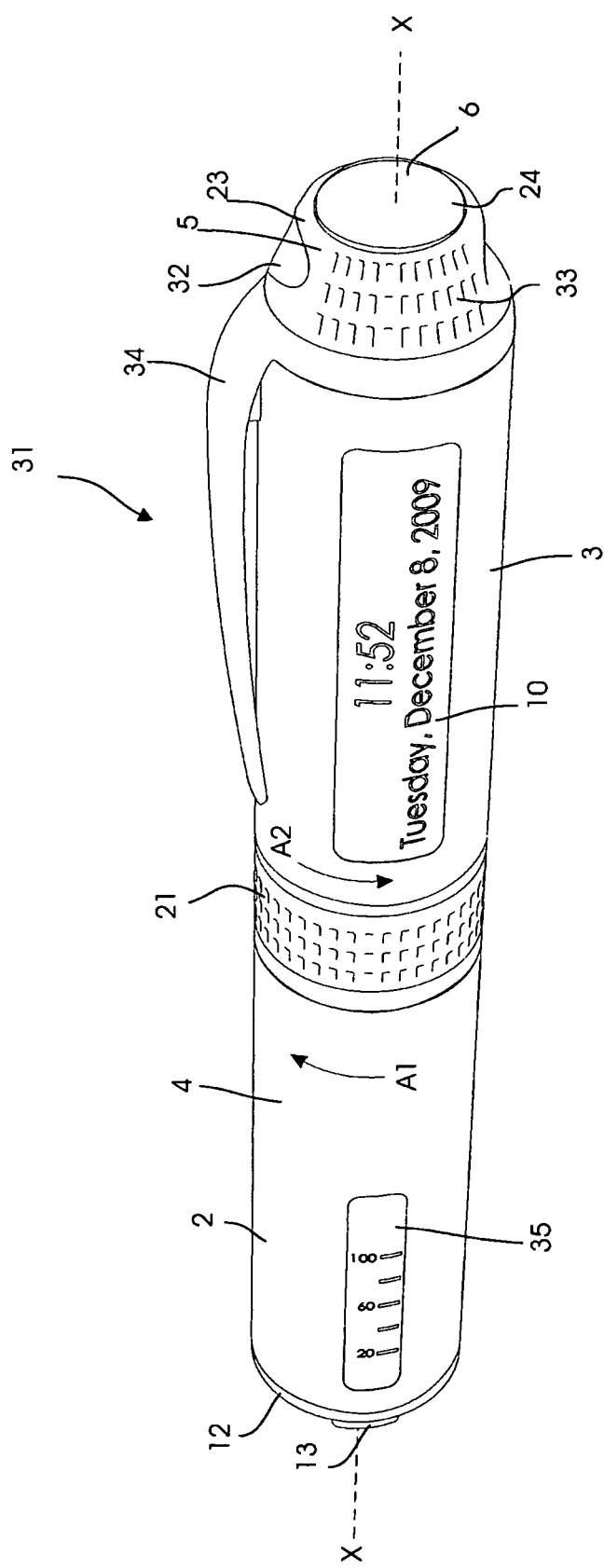
FIG. 3 shows, seen in perspective, the exterior design of a pen-shaped apparatus according to the present invention.

FIG. 3 is a perspective view, seen oblique from the exterior end part 5 of the actuation means 5,6, of the exterior design of a pen-shaped apparatus 31 according to the present invention for use by diabetics in monitoring the blood glucose concentration and administering insulin by injecting a suitable dose of insulin in response to a determination of the actual glucose concentration. The pen 31 is configured to right hand use in the presentation shown.

The main parts of the pen 31 are substantially the same as for the previously described embodiments 1; 22 and for like parts same reference numerals are used. The pen-shaped apparatus 31 is in the following description designated a pen for use by diabetics. This designation is not intended to limit the scope of the present invention and other treatment and administration regimes than for diabetes and exterior designs are foreseen, including for example disc-shaped designs in which case the functionalities of ejecting and retracting lancets 16 and glucose strips 15 and injection needles 18 can be made along the circumference of two individually rotatable disc parts. The large surfaces of a disc present a conveniently large surface for electronic interactions with the functionalities. Asthma may be mentioned as an example of another disease that may be treated. For use with asthma the portable apparatus could includes an exhaler or inhaler, and means for determining a parameter in exhaust air or blood from the patient. A spirometer may also be incorporated in combination with other components and parts already described above enclosed in a common housing.

The pen 31 has first part 3, a second part 4, a rotations ring 21, an actuator 5 having an exterior end part 5 consisting of a rotation knob 23 and a depressible function knob 24. As indicated with the arrows A1, A2 the first part 3 and the second part 4 can be rotated in opposite directions. The rotation knob 23 has opposing finger abutment cavities or depressions 32 (only one shown in the FIG.) to allow the user to get a firm grip in said rotation knob 23. The rotation knob 23 further has an irregular surface for making it tactile; in the case shown irregularities are concentric rings of rectangular indents 33.

The first part 3 of the pen 31 has a clip 34 for attaching or hanging the pen 31 in for example a breast pocket, a belt or a case.

The second part 4 has a scale 35 which enables the user to monitor the dose of injection medium the pen 31 has been configured to inject.

The pen 31 is illustrated in the stand by functionality mode and the data on the display 10 is the date and the clock, as exemplary indicated.

Figure 4:
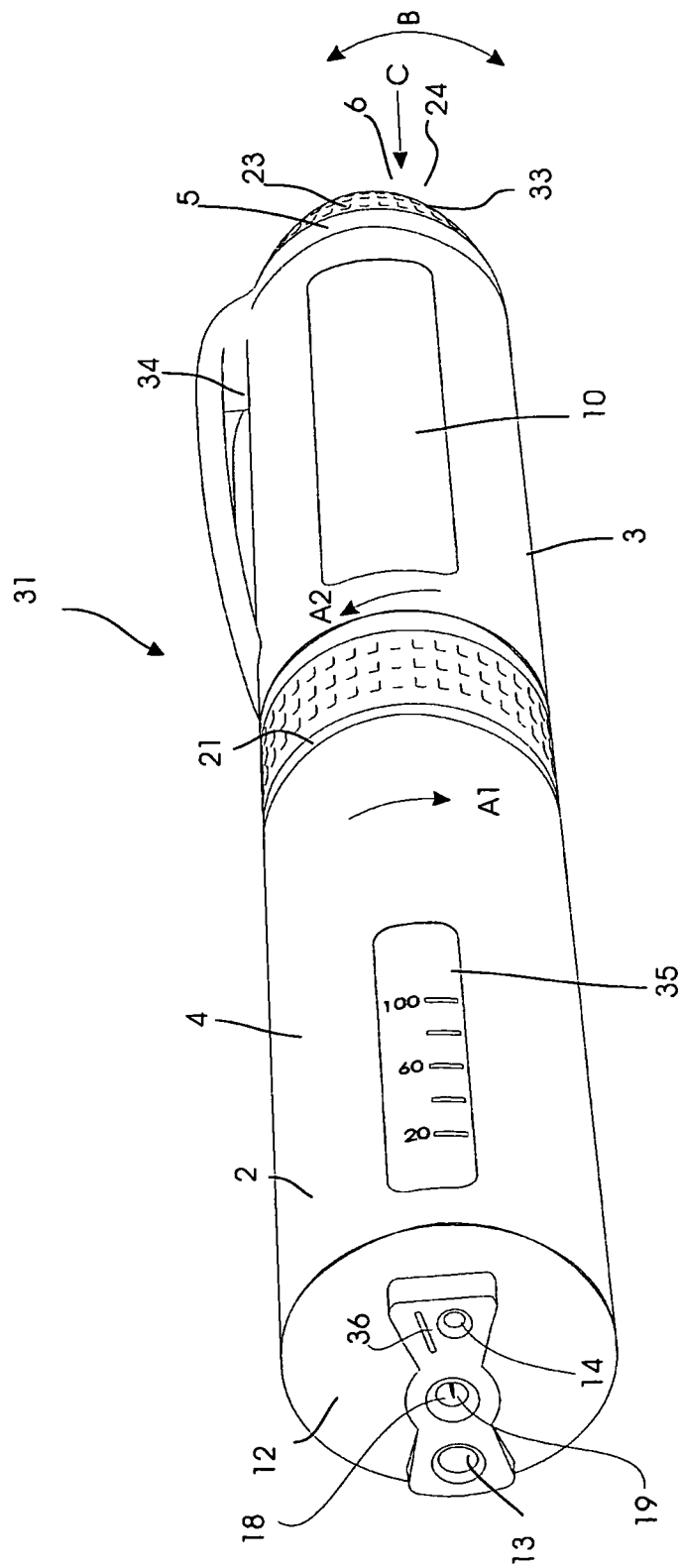
FIG. 4 shows the embodiment in FIG. 3 in the sampling mode.

FIG. 4 shows in perspective the pen 31 in a sampling mode. The pen 31 is seen oblique from the operating end 12 of the second part 4 and the sampling mode is reached by rotating the rotation knob 23 as indicated with the arrow B. The bulb 13 it lit and the tip of a lancet is exposed from the first opening 14 in the operating end 12 of the second part 4 of the common housing 2. The tip of the lancet 16 is ejected by depressing the function knob 24 as indicated with the arrow C. The lancet strength or lancing force is set to a factor, which the user has selected as being appropriate. The display 10 could e.g. indicate the selected depth, which the user empirically has found out provides a suitable size of blood drop. The operating end 12 of the second part 4 further has a slot 36 for ejecting a test area 37 of a test strip 16.

Figure 5:
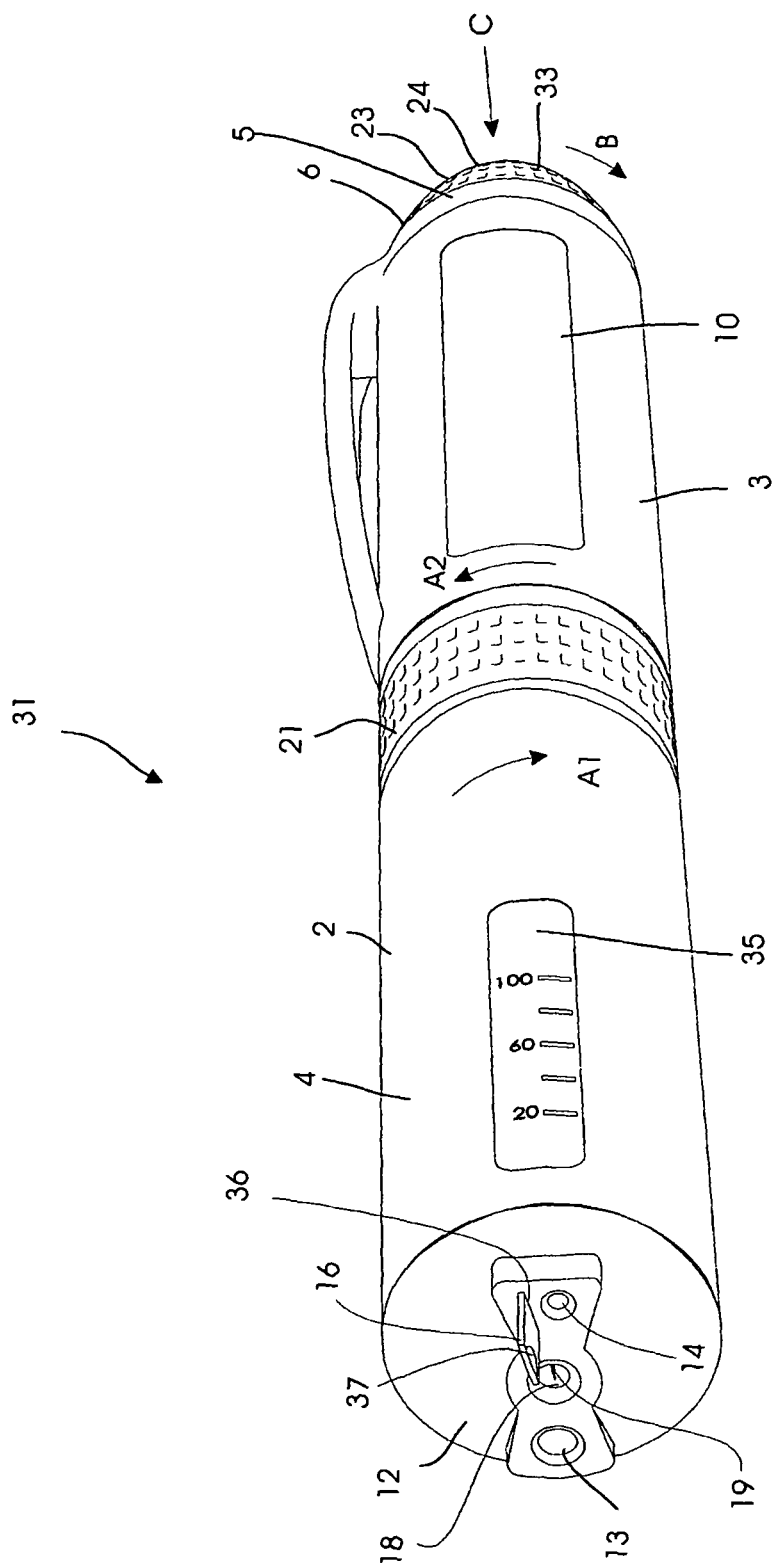
FIG. 5 shows the embodiment in FIG. 3 in the determining mode.

In FIG. 5 the pen 31 is now configured to the determining mode and a test strip 16 has been exposed from the slot 36. The first opening 14 and the slot 36 may in the alternative be the same opening. By means of the integrated analyzer A the glucose concentration is determined and indicated on the display 10 to allow the user to go to the injection mode and adjust the amount of insulin to be injected to keep the blood glucose concentration under control.

Figure 6:
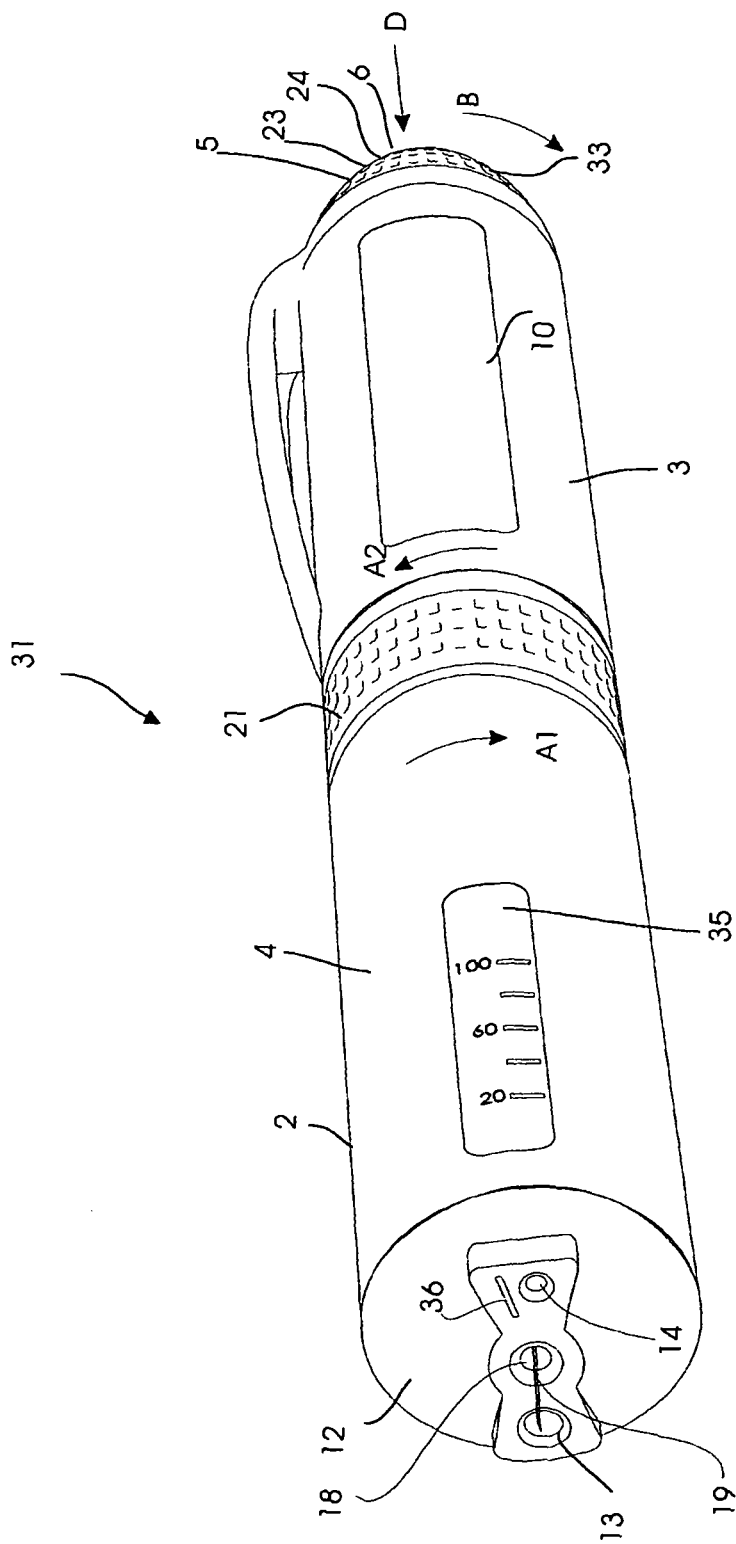
FIG. 6 shows the embodiment in FIG. 3 in the injection mode.

In FIG. 6 the pen 31 is shown in the injection mode and the tip of the injection needle 19 is exposed through the second opening 18 by activating the function knob 24. Optionally, as indicated with the arrow D, a second activation of the function knob 24 may be required for actually performing the injection into the object subsequent to exposing the injection needle.

Figure 7:
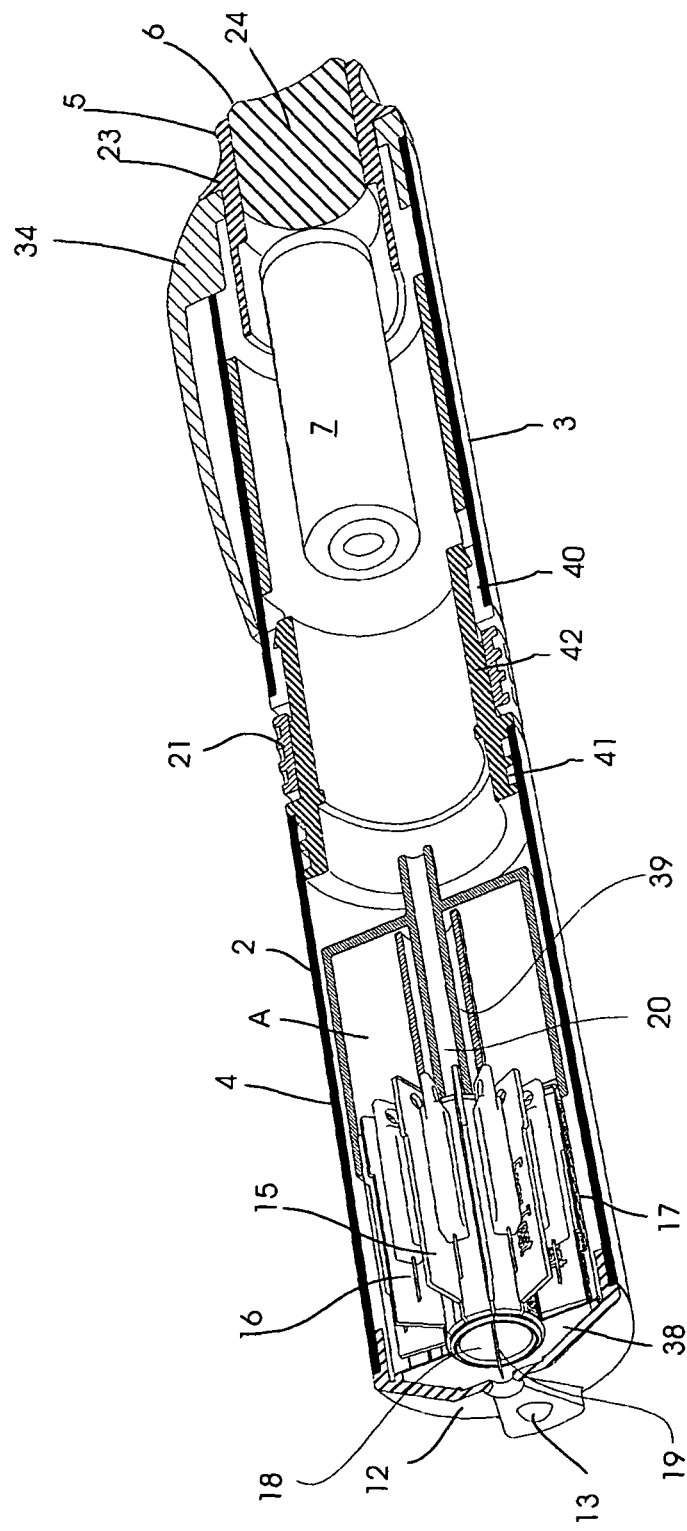
FIG. 7 shows the pen-shaped apparatus shown in FIG. 3 in a lengthwise sectional view into the interior of the common housing, including the arrangement of a cartridge.

The interior arrangement of the cartridge 17 and the rotational relationship between the first part 3 and the second part 4 of the common housing 2 is seen in the longitudinally intersected pen 31 shown in FIG. 7. Switching means part, such as sensors, and actuation means parts, such as motors or hooks, as well as the processing unit and any wiring and electronic lines are left out to better overview the rotational functionality between the first part and the second part to shift between functionality modes are not shown.

The cartridge 17 defines a circumferential wall chamber 38 in which the test strips 15 and the lancets 16 is circumferentially and alternately distributed. In use the actuation means revolves or rotate the cartridge one or more times depending on functionality mode to locate a test strip or a lancet in front of the first opening 14 in the operating end of the second part 4, which is a unit opening 14 for ejecting either the test strip 15 or the lancet 16. The operating end may have separate ejecting openings for test strip 15 and lancet 16, namely the slit 36 and the first opening 14, respectively. The function button 24 is depressed and either a test strip 15 or a lancet 16 is ejected for use through the appropriate opening. The circumferential wall chamber 38 defines a through going bore chamber 39 inside which the medicament ampoule 20 is located and connected to the injection needle 19.

The first part 3 and the second part 4 of the common housing is in rotational engagement with each other by means of engaging screw threads on contacting ends part. Thus the first part 3 has a threading 40 and the second part 4 has a threading 41 in mutual operative rotational communication via a threaded connection member 42, which screw threads 40,42 together with one or more sensors (not shown) constitutes the main parts of the switching means for switching between different functionality modes.

Figure 8A:
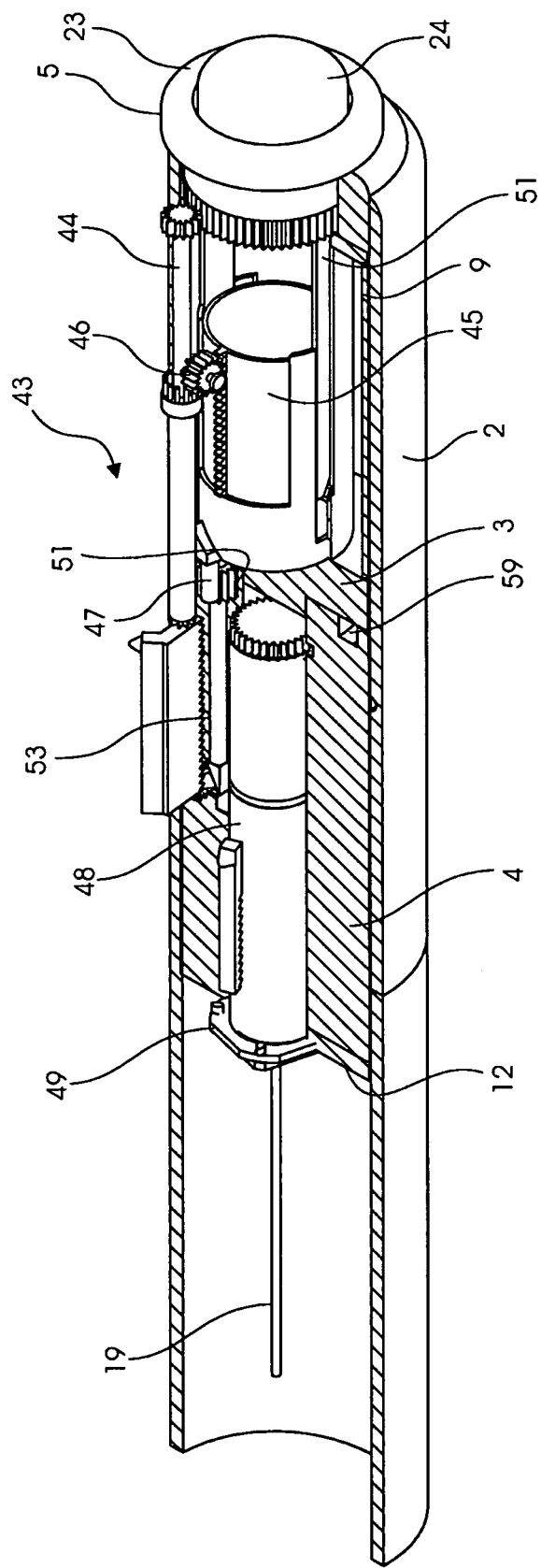
FIG. 8a, b shows a lengthwise sectional view of the interior of the common housing in an alternative embodiment of the pen-shaped apparatus according to the present invention.
Figure 8B:
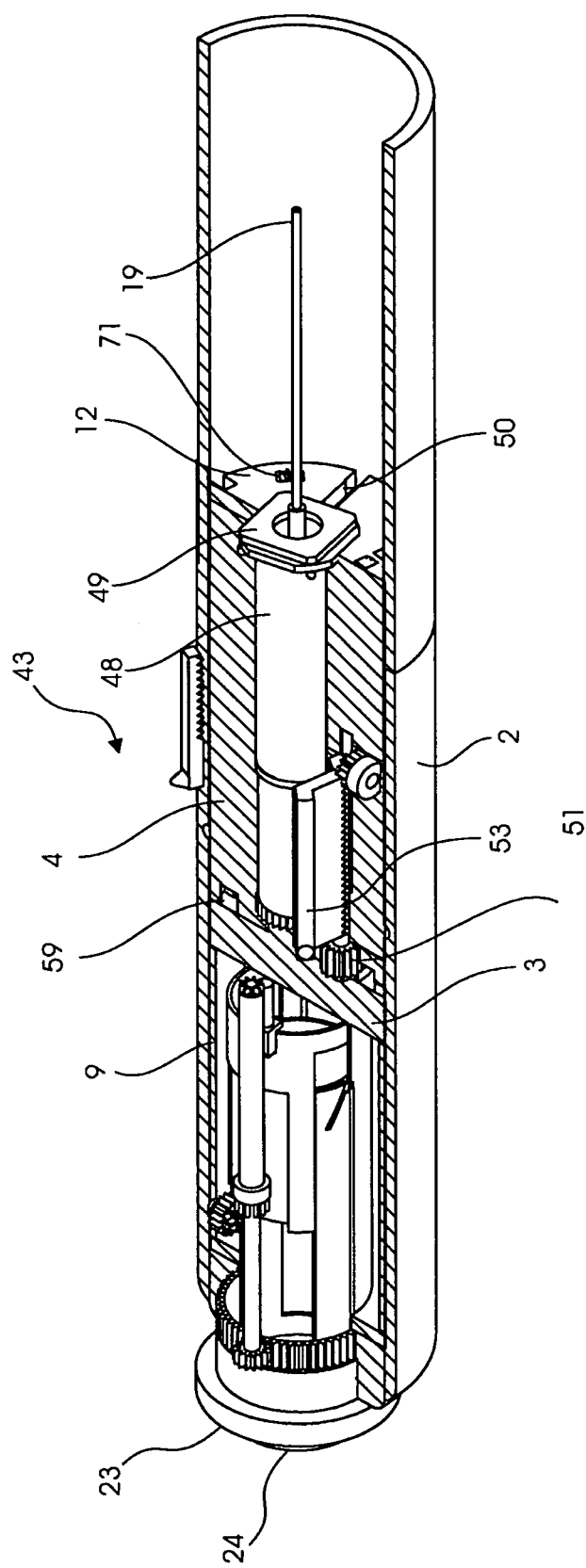

FIGS. 8a and 8b illustrates an alternative embodiment of a pen-shaped apparatus 43 according to the present invention in the stand by mode.

FIG. 8a is a perspective view, seen oblique from the exterior end part 5 of a pen-shaped apparatus 31 according to the present invention, and FIG. 8b shows the same from the operating end 12.

It is presently assumed that the pen 43 is used for monitoring the blood glucose concentration and administering insulin by injecting a suitable dose of insulin in response to a determination of the actual glucose concentration. In order to meet the requirements of the user in this respect the pen 43 has five different functionality modes: the off mode, the sampling mode or lancer mode, the determining mode or test strip mode, the injection mode and the PDA/cartridge rotation mode, however the actual number of functionality modes can, within the scope of the present invention, be both higher and lower.

The main parts of the pen 43 are substantially the same as for the previously described embodiments 1; 22; 31 and for like parts same reference numerals are used.

The main parts are an elongated, tubular, common housing 2, defined by a first part 3 and a second part 4. The first part 3 has an exterior end part 5, which is a part of the actuation means and is consisting of a rotation knob 23 and a depressible function knob 24. The rotation knob 23 can advantageously have e.g. finger abutment cavities or depressions (not shown) to allow the user to get a firm grip on said knob.

A power source in the form of a battery (not shown) for powering the apparatus 43 is disposed inside the first part 3. The first part 3 also houses an electronic compartment 9 for the different electronics including the processing unit, i.e. the CPU and the determining means. This electronic compartment is in electronic communication with the relevant parts of the apparatus enabling mechanical control and electronic communication with said parts.

The first part 3 also comprises a multi-feeder 44 arranged for transferring rotational force to the different mechanical parts when the pen 43 is in the different functionally modes.

A pressure part 45 connected to the depressible function knob 24 is placed in the hollow spacing of the first part 3 and is arranged to activate a firing pin 47, which depending on the respective functionality modes activates different mechanical parts in the second part 4.

The first part 3 extends into the second part 4, which second part 4 terminates in an operating end 12 having a groove 50. The outer housing 2 extends beyond the operation end 12 with the injection needle 19 in order to protect the user from accidental needle pricks when the pen 43 is not in use.

The second part 4 also comprises a cartridge (not shown) housing the test strips and lancets. The cartridge could have any relevant design, but e.g. the design of the cartridge 17 in FIG. 7.

A combined needle holder/injection function arm 48 holding the injection needle 19 in place is also placed in the second part 4. The injection needle is in communication with a medicament ampoule or vial 20 also located inside said second part 4. The injection needle 19 is securely fastened to the combined needle holder/injection function arm 48 via a needle-fastening lid 49.

The switching between the different modes is enabled by rotating the first part 3 and the second part 4 in relation to each other. As five different functionally modes are present in the respective embodiment the rotation is ⅕ of the circumference of the pen 43, however other rotation relationships will also be within the scope of the invention.

The switching between the different modes is effectuated via a groove (not shown) in the upper outer housing 2. This groove is a straight line around the pen 43 except for a small part where the groove goes down towards the second part. As will be evident in the following the groove will allow mechanical parts in communication with said groove to be dragged down, rotated or in order ways moved or affected, in order to ensure that a motion, force or signal is transferred to other mechanical and/or electronic parts in communication with said mechanical part, whereby the desired functionality mode is obtained.

The different parts of the pen 43 will be explained in detail in relation to their involvement of the different functionality modes.

Figure 9:
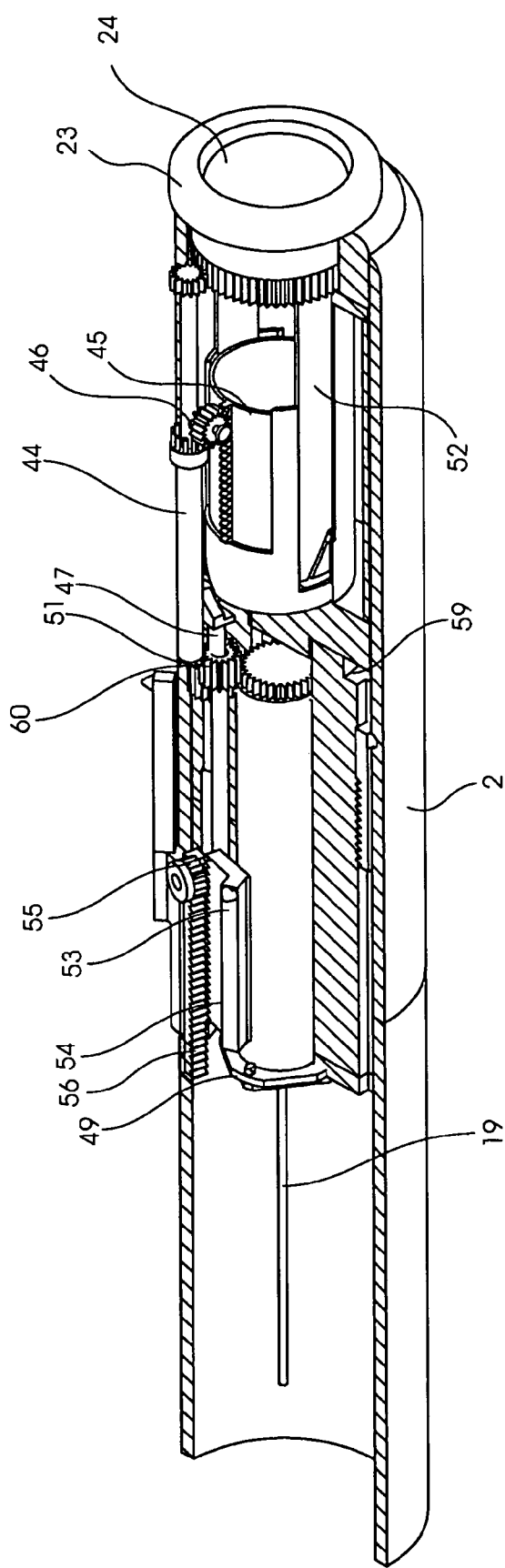
FIG. 9 shows the embodiment in FIG. 8 in the sampling mode.

FIG. 9 shows in perspective the pen 43 in the lancer mode or sampling mode. The sampling mode has been reached by rotating the first and second part 3,4 in relation to each other ⅕ of the circumference of the pen 43, in the direction indicated by the arrow B.

During said rotation the trench in the housing 2 will force the lancer function arm 54 down to a lower position in the housing. During this movement the lancer function arm 54 will transfer its motion/force via the charging/firing cog 55 to the lancer ejection rod 56 drawing the rod 56 towards the operating end 12. This will provide stretching/tensing of a spring (not shown) placed between the lancer ejection rod 56 and the lancer strength settings arm 57. Simultaneously, the lancer function arm 54, which is in communication with the CPU, will activate the lancer mode of the CPU.

The rotation will also force the multi-feeder 44 to travel via the circular trench 59 in the second part 4 until it reaches its predetermined position. At said position the multi-feeder 44 connects with the upper transfer lancer cog 51 which in turn connects to the lower transfer lancer cog 60. The lower transfer lancer cog 60 has "screw"-tracks on its inner hole where the lancer strength settings arm 57 is connected.

As a rotational force to the rotation ring 25 is transferred via the multi-feeder 44 and the upper transfer lancer cog 51 down to lower transfer lancer cog 60 it is possible for the user to control the tension of the spring (not shown) placed between the lancer ejection rod 56 and the lancer strength settings arm 57. This is due to the fact, that since the lancer strength settings arm 57 has helicoidal grooves that matches those on the inner hole of the lower transfer cog 60 a rotation of the lower transfer cog 60 will adjust the lancer strength settings arms 57 position, and thereby controlling how stretched the spring placed between the lancer ejection rod 56 and the lancer strength settings arm 57 is, and thereby be able to adjust the lancing force and the penetration strength of the lancer in a continuous fashion, simply by rotation the rotation knob 23.

In order to eject the lancer, the user simply then presses the functionality knob 24. This will force the pressure part 45 to rotate the firing ring 52 which then will presses down the firing pin 47. The firing pin has a spring beneath it (not shown) in order to force the firing pin upwards, which in turn force the lancer firing pin 53 in the second part 4 down via the upper transfer lancer cog 51.

When the lancer firing pin 53 is pressed down it will force the charging/firing cog 55 to release its connection between the lancer function arm 54 and lancer ejection rod 56, whereby the lancer ejection rod 56 forcefully will be ejected by the spring (not shown).

This force will in turn be transferred to the currently ready lancer in the cartridge (not shown) shooting it out enabling the user to prick his/her skin in order to obtain the desired drop of blood.

Figure 10:
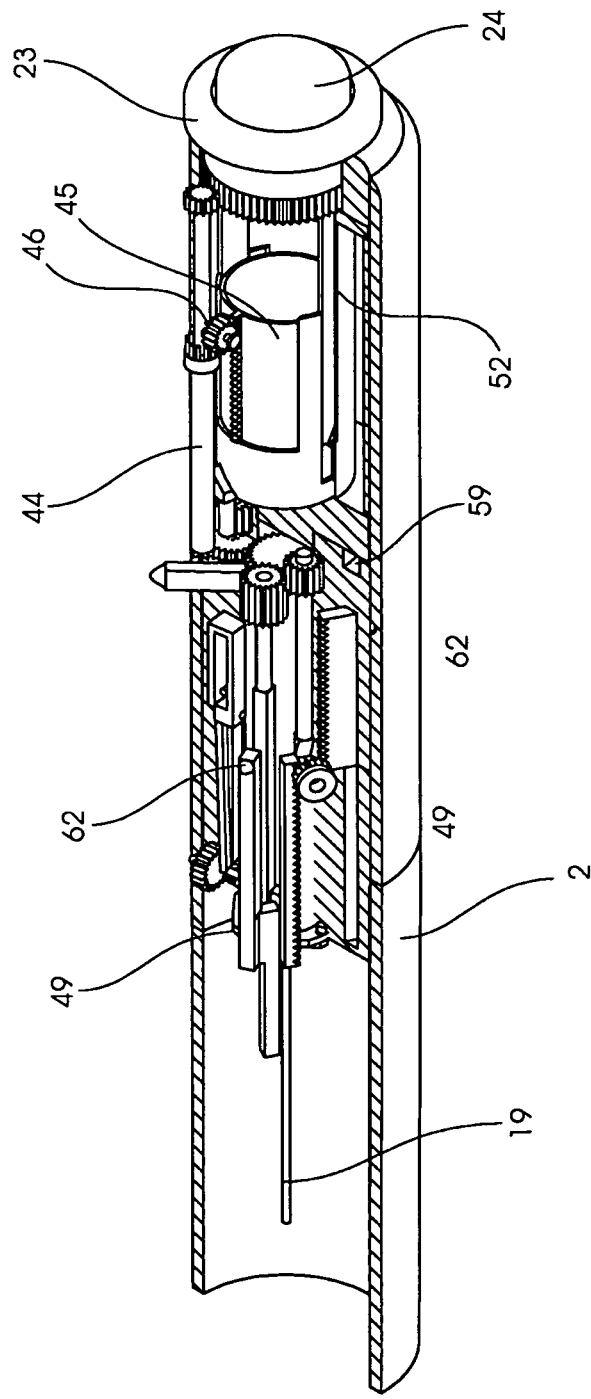
FIG. 10 shows the embodiment in FIG. 8 in the determining mode.

In FIG. 10 the pen 43 is now configured to the determining mode by rotating of the first and second part 3,4 another ⅕ of the circumference of the pen 43, in relation to each other in the direction indicated by the arrow B.

During said rotation the trench in the housing 2 will force the test strip function arm 62 down to a lower position in the housing. During this movement the test strip function arm 62 will eject a test strip from the cartridge (not shown) and connect it with the determining means and activate the test strip mode in the CPU.

Figure 11:
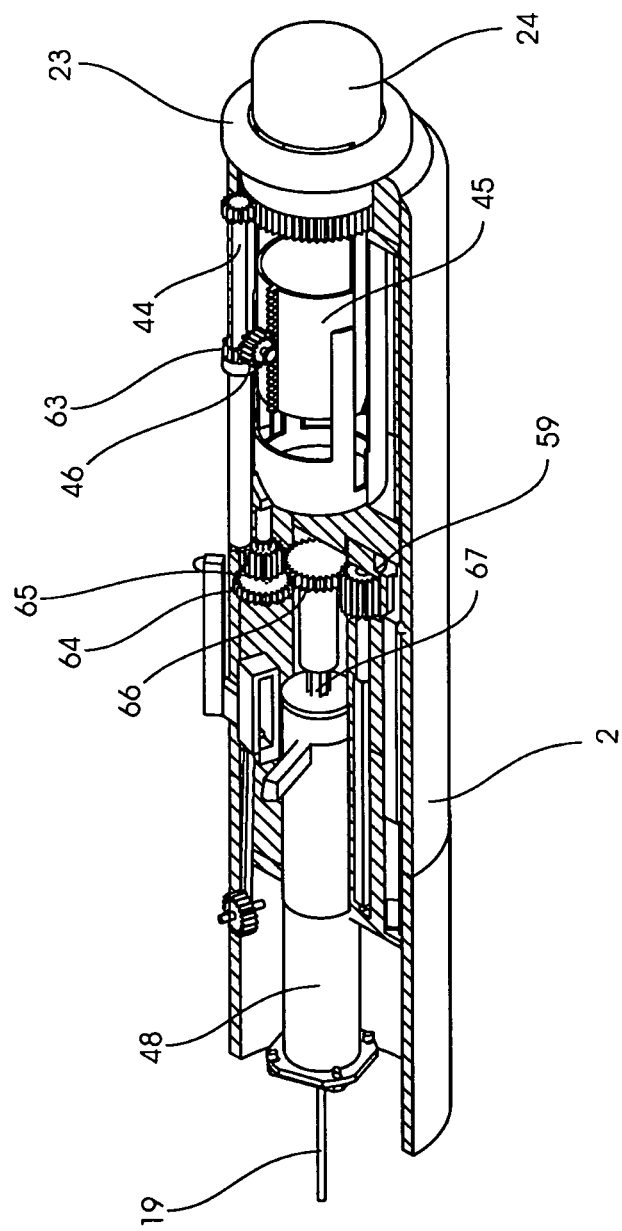
FIG. 11 shows the embodiment in FIG. 8 in the injection mode.

In FIG. 11 the pen 43 is shown in the injection mode. The injection mode has been reached by rotating the first and second parts an additional ⅕ of the circumference of the pen 43, in relation to each other in the direction indicated by the arrow B.

During said rotation the trench in the housing 2 will force the combined syringe holder and injection function arm 48 to be pressed down towards the operating end 12, thereby ensuring that the needle 19 will extend trough a hole in the cartridge (not shown) and outside of the pen 43's housing 2, making it possible to inject the needle into the subject.

When the injection mode is reached the user can raise the function knob 24 by rotating the rotation knob 23. During the rotation to reach the injection mode the multi-feeder 44 will follow the circular trench 59 where it will meet an elevation forcing the multi-feeder 44 to be raised. The raised multi-feeder 44 ensures that the multi-feeder cog 63, placed on the multi-feeder 44, can connect to the transfer cog 46, which will generated a rotational force on pressure part 45, which in turn raises the function knob 24 as seen in FIG. 11.

The rotation to reach the injection mode will also move the multi-feeder 44 in the circular trench 59 in the second part 4 until the multi-feeder reaches its predetermined place where it connects with the upper transfer injection cog 58. This cog rotates freely without affecting the lower transfer injection cog 64 until the dosage transfer pin 65 is pressed down by the firing pin 47.

In order to eject the medicament the user presses the function knob 24, whereby the firing pin 47 will be pressed down into the second part 4 of the pen 43. Here the pin 47 will force the dosage transfer pin 65 to connect the upper and lower transfer injection cogs 58, 64 hence transferring the rotational force from the multi-feeder 44 to the lower transfer injection cog 64.

As the function knob 24 is continuously pressed down the pressure part 45 will transfer rotational force to the multi-feeder 44 until the pressure part 45 hits its bottom position. Hence the lower transfer injection cog 64 will only rotate in one direction. The rotation of cog 64 will provide rotation of the top dosage cog/pin 66, which in turn will rotate the lower dosage pin/syringe connector 67. As the top dosage cog/pin 66 and the lower dosage pin/syringe connector 67 can extend without loosing its rotational capacity it is possible to use different sized syringes in the same unit.

Figure 12:
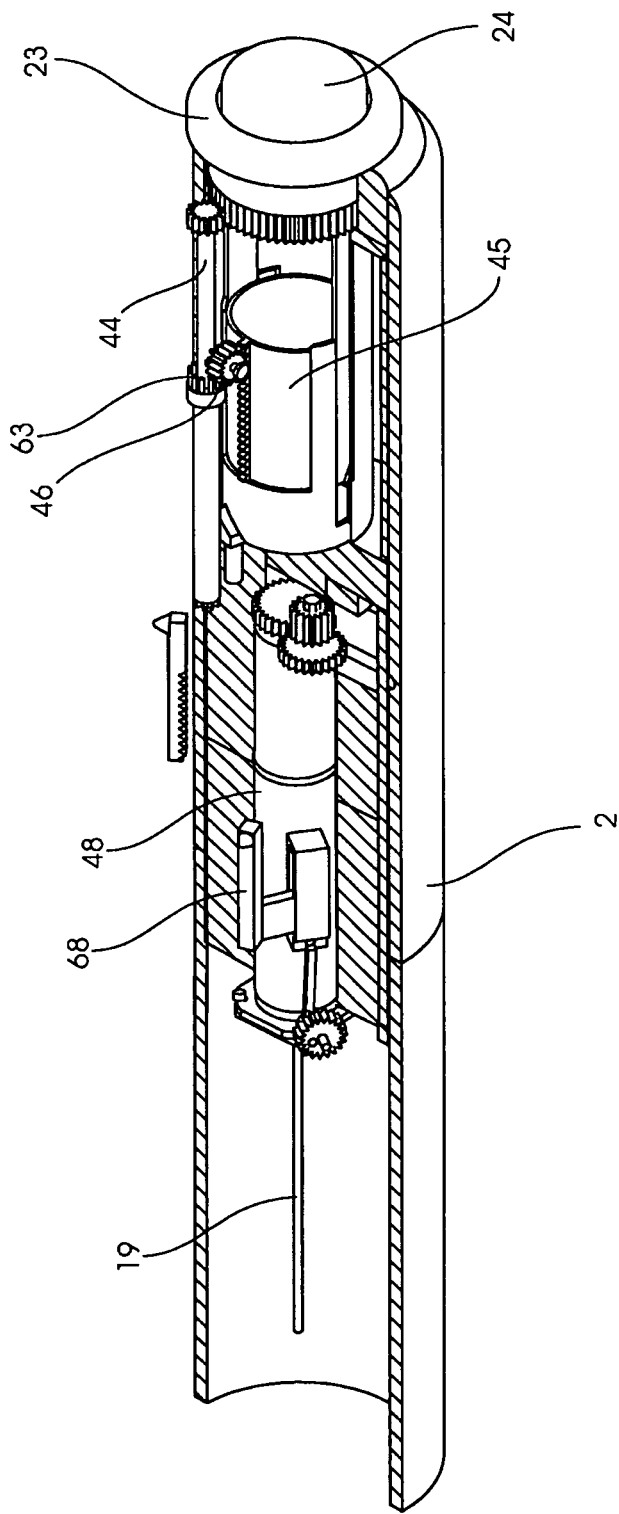
FIG. 12 shows the embodiment in FIG. 8 in the PDA-cartridge feed mode.

In FIG. 12 the pen 43 is shown in the Personal Digital Assistant (PDA)-cartridge feeder mode. This mode has been reached by rotating the first and second parts an additional ⅓ of the circumference of the pen 43, in relation to each other, in the direction indicated by the arrow B.

During said rotation the trench in the housing 2 will force the cartridge upper feeder arm 68 to be pressed down. This will in turn force the cartridge lower feeder arm 69 down which in turn will move the cartridge feeder rod 70 down which will in a piston-like manner rotate the cartridge feeder wheel 71. As this wheel 71 extends outside of the second part 4, as best seen in FIG. 8b, it connect to a track on the cartridge making it rotate a predetermined length hence aligning a fresh lancer and test strip in the cartridge for the next time the device will be used.

The stand by mode is obtained by rotating the first and second parts an additional ⅓ of the circumference of the pen 43, in relation to each other, in the direction indicated by the arrow B.

In summary the apparatus according to the present invention is an all-in-one device that facilitates the medical treatment process for patients, medical professionals and/or other people in other professions due to improvements in the following areas of portability, the fact that only a single pocketsized device has to be carried, operated and maintained instead of several devices, and that a unified user interface to access and switch between the different sets of functionality is used. The apparatus may be produced based upon all or a subset of the above mentioned novelty features.

The apparatus according to the present invention may also adapt its behavior and functionality depending on the type of exchangeable components, thereby decreasing the risk for human errors. Thus the inventive apparatus is provided with electronic tagging of exchangeable components.

Emphasis is made that the embodiments shown in the drawings illustrates exemplary embodiments which is not intended to limit the broad scope of possible modifications and variants covered by the scope of the appended claims.

The multi-function portable apparatus according to the present invention is operated by selecting one functionality mode at a time. These functionality modes may be accessed by rotating two main parts of the apparatus in opposite directions. The list of functionality modes is adapted to fit the application area of the apparatus which means that the list presented in the following represents only one of many possible solutions. The list may consist of duplicates, replacements, eliminations and additions and it may also be rearranged. For each functionality mode, the user interface may change to better fit with different situations. One such important interface change due to functionality mode switching is the multi function knob/button 23,24, which functionality is adapted to each mode as described in the following. In addition to the multi function knob/button 23,24, a navigation rotation ring 21 is used for human-apparatus communication. For instance, the graphical user interface, the display 10, may be operated using this input method. This input component, navigation rotation ring 21, may be used to scroll upwards and downwards, and can also be pressed sidewise to the left or right direction when holding the apparatus.

Example of Combination of Functionality Modes a. Stand by mode:
  A power saving mode. A key lock may be activated to operate the apparatus again.

b. Sampling mode:
  The lancet is loaded using the actuation means and is ready to use. The display is activated and the function knob of the multi-functional knob/button is depressed to perform lancing. by rotating the rotation knob of the multi-functional knob/button the lancing power or lancet strength is adjusted. If more sample is needed the user steps back and forth again to reload the lancet.

c. Determining mode:
  Testing components are ready to be used within the sample analyzer, e.g. a body fluid analyzer such as a glucose meter, without any further action. The test strip is presented and ready to be used. The display is activated. If more blood is needed, the user steps back to the sampling mode where the lancet is ready to be used, and takes a new sample.

d. Injection mode:
  The injection needle to be used for injection of injection medium, such as a medication like insulin, is presented and ready to be used. The display is activated. To inject the selected dosage of medicine the user simply presses the multifunction knob/button. Rotating the same knob/button may adjust the volume of medicine to be injected.

e. Information mode:
  The information mode is used for information management by browsing through stored information and access additional functionality. The display is activated. In this mode the user can access his/her personal information and benefit from the additional applications and functionalities.

Other functionalities may include the additional features and functionalities already mentioned above. Intended yet other functionalities and features that might be integrated or incorporated in the apparatus according to the present invention may also include the non-exhaustive list of:

Thermometer and temperature warnings.
Time and/or information based alarms, alerts and warnings.
Speaker and/or other signaling components.
Left-hand mode/right-hand mode setting.
Memory for track keeping, personal profiles and personalization.
Personal digital assistant
(PDA) functionality.
Connectivity with other devices, e.g. computers, mobile devices such as PDA's, cell phones and media players, and other medical equipment.
Add-ons, e.g. pedometer, media player, flashlight, docking stations, clip-on shells, etc.

What is claimed is:

1. A portable medical apparatus comprising:
   a lancet for, in a sampling mode, making a prick, lesion or incision to expose at least one sample of a fluid from an object;

at least one test strip for, in a determining mode, determining at least one parameter of the exposed fluid sample;

an injector for, in an injecting mode, performing at least one injection of an injection medium, wherein the lancet, test strip(s), and injector are separate devices that are operable independently of each other;

a single common housing for encasing at least the lancet, test strip(s), and injector, the common housing comprising a hollow body having a first part and a second part;

a switch configured to be rotatable with the first part and second part in opposite directions for switching between the sampling, determining and injection modes for exposing the lancet, test strip(s), and injector, respectively; and actuation means for individually actuating each of the lancet, test strip(s), and injector, wherein the first part of the common housing includes an exterior part of the actuation means, and has an end opposite to the exterior part of the actuation means that is in operative communication with the second part, wherein the second part has an operating end from which the injector is exposed along or about a longitudinal axis of the common housing and from which the lancet or test strip(s) is/are exposed in a direction along an axis radially spaced from the longitudinal axis, wherein the injector and lancet are configured to be exposed via separate openings, and wherein at least the lancet, test strip(s) and injector are located in the common housing alongside or concentric to each other.

2. The portable medical apparatus according to claim 1, wherein the actuation means includes one or more motors for the lancet and injector for individual operation of the lancet and injector.

3. The portable medical apparatus according to claim 1, wherein the actuation means includes one or more motors for the lancet, test strip(s) and injector for individual operation of each.

4. The portable medical apparatus according to claim 1, which further comprises a processing unit for controlling the lancet, test strip(s) and injector in the respective sampling, determining and injection modes.

5. A portable medical apparatus comprising:
functionality modes including:
a sampling mode for sampling at least one sample of a fluid in an object, a determining mode for determining at least one parameter of an exposed fluid sample, and an injecting mode for performing at least one injection of an injection medium, wherein the sampling, determining and injection modes are operable independent of each other, and components for carrying out the functionality modes, including:

a lancet for, in the sampling mode, making a prick, lesion or incision to expose at least one sample of a fluid from an object, at least one test strip for, in the determining mode, determining the at least one parameter of the exposed fluid sample, and an injector for, in the injecting mode, performing at least one injection of an injection medium, wherein the lancet, test strip(s), and injector are operable independent of each other, a single common housing for encasing at least the lancet, test strip(s), and injector, the common housing comprising a hollow body having a first part and a second part, a switch configured to be rotatable with the first part and second part in opposite directions for switching between the sampling, determining and injection modes for operating exposing the lancet, test strip(s), and injector, respectively, a processing unit for controlling operation of the functionality modes of the apparatus; and actuation means for individually actuating each of the lancet, test strip(s), and injector, wherein the first part of the common housing includes an exterior part of the actuation means, and has an end opposite to the exterior part of the actuation means that is in operative communication with the second part, wherein the second part has an operating end from which the injector is exposed along or about a longitudinal axis of the common housing and from which the lancet or test strip(s) is/are exposed in a direction along an axis radially spaced from the longitudinal axis, wherein the injector and lancet are configured to be exposed via separate openings, and wherein at least the lancet, test strip(s) and injector are located in the common housing alongside or concentric to each other.

6. The portable medical apparatus according to claim 5, wherein the actuation means is configured for adjusting lancing force and depth, launching the lancet, adjusting a dosage of the injection medium, and injecting the injector.

7. The portable medical apparatus according to claim 6, wherein the actuation means includes an adjusting member of a knob, button or motor.

8. The portable medical apparatus according to claim 5, wherein the processing unit establishes an appropriate dose of injection medium to be injected by the injector.

9. The portable medical apparatus according to claim 5, wherein the end opposite the exterior part is physically connected to the second part via at least the switch.

10. The portable medical apparatus according to claim 5, wherein the switch comprises at least one sensor for registering switching between the sampling mode, the determining mode, and/or the injection mode.

11. The portable medical apparatus according to claim 5, further comprising a power source in the form of a battery for powering the apparatus and a display, wherein the display is in electronic communication with the processing unit, and the processing unit controls the lancet, test strip(s) and injector in the respective sampling, determining and injection modes, and provides for displaying displayable information.

12. The portable medical apparatus according to claim 11, wherein the displayable information comprises data selected from the group consisting of functionality mode, date, clock, the determined parameter, an indication reflecting the status or level of the parameter, medium amount to be injected in response to the determined parameter, user information, apparatus status, power level of the power source and combinations thereof, and wherein the determined parameter is the user's glucose concentration and is displayed to allow the user to select the injection mode and adjust an amount of insulin to be injected to control the user's glucose concentration.

13. The portable medical apparatus according to claim 5, further comprising illumination means.

14. The portable medical apparatus according to claim 5, which further comprises a rotation ring in operative communication with the components of the apparatus for carrying out the functionality modes.

15. The portable medical apparatus according to claim 14, wherein the rotation ring is operable along a longitudinal axis of the common housing in at least one longitudinal direction or is rotatable about the longitudinal axis in at least one rotational direction.

16. The portable medical apparatus according to claim 5, wherein at least the lancet and at least a part of the test strip or strips are combined in a replaceable cartridge configured to be accommodated in the second part of the common housing.

17. The portable medical apparatus according to claim 5, wherein the actuation means includes one or more motors for actuating the lancet, the test strip(s) and/or the injector.

18. A portable medical apparatus comprising:
functionality modes including:
a sampling mode for sampling at least one sample of a fluid in an object, a determining mode for determining at least one parameter of an exposed fluid sample, and an injecting mode for performing at least one injection of an injection medium, wherein the sampling, determining and injection modes are operable independent of each other, and
components for carrying out the functionality modes, including:
a lancet for, in the sampling mode, making a prick, lesion or incision to expose at least one sample of a fluid from an object,
at least one test strip for, in the determining mode, determining the at least one parameter of the exposed fluid sample, and
an injector for, in the injecting mode, performing at least one injection of an injection medium, wherein the lancet, test strip(s), and injector are operable independent of each other,
a rotation ring in operative communication with one or more of the lancet, test strip, or injector,
a single common housing for encasing at least the lancet, test strip(s), and injector, the common housing comprising a hollow, generally cylindrical body having a first part and a second part,
a switch configured to be rotatable with the first part and second part in opposite directions for switching between the sampling, determining and injection modes for exposing the lancet, test strip(s), and injector, respectively,
a processing unit for controlling operation of the functionality modes of the apparatus; and
actuation means for individually actuating each of the lancet, test strip(s), and injector and for adjusting lancing force and depth, launching the lancet, adjusting a dosage of the injection medium, and injecting the injector,
wherein the first part of the common housing includes an exterior part of the actuation means, and has an end opposite to the exterior part of the actuation means that is in operative communication with the second part,
wherein the second part has an operating end from which the injector is exposed along or about a longitudinal axis of the common housing and from which the lancet or test strip(s) is/are exposed in a direction along an axis radially spaced from the longitudinal axis,
wherein the end opposite the exterior part is physically connected to the second part via at least the switch,
wherein the injector and lancet are configured to be exposed via separate openings, and
wherein at least the lancet, test strip(s) and injector are located in the common housing alongside or concentric to each other.

19. The portable medical apparatus according to claim 18 further comprising a power source in the form of a battery for powering the apparatus, the power source disposed inside the first part, and a display for displaying information comprising data selected from the group consisting of functionality mode, date, clock, the determined parameter, an indication reflecting the status or level of the parameter, medium amount to be injected in response to the determined parameter, user information, apparatus status, power level of the power source and combinations thereof.

* * * * *

UNITED STATES PATENT AND TRADEMARK OFFICE
CERTIFICATE OF CORRECTION

PATENT NO. : 9,737,253 B2  
APPLICATION NO. : 12/674363  
DATED : August 22, 2017  
INVENTOR(S) : Fonduca et al.

Page 1 of 1

It is certified that error appears in the above-identified patent and that said Letters Patent is hereby corrected as shown below:

On the Title Page

Insert the following before Item (65), Prior Publication Data:
-- Related U.S. Application Data
(60) Provisional application No. 60/968,763, filed on Aug. 29, 2007. --.

In the Specification

Column 20:
Line 8, before "exposing", delete "operating".

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*